(12) United States Patent
Schiele et al.

(10) Patent No.: US 10,123,834 B2
(45) Date of Patent: Nov. 13, 2018

(54) SURGICAL INSTRUMENT COMPRISING AN IMPROVED ACTUATING DRIVE

(71) Applicant: Erbe Elektromedizin GmbH, Tuebingen (DE)

(72) Inventors: Elias Schiele, Tuebingen (DE); Tobias Amann, Gieslingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 578 days.

(21) Appl. No.: 14/482,901

(22) Filed: Sep. 10, 2014

(65) Prior Publication Data

US 2015/0073394 A1 Mar. 12, 2015

(30) Foreign Application Priority Data

Sep. 10, 2013 (EP) .................................... 13183639
Sep. 12, 2013 (EP) .................................... 13184190

(51) Int. Cl.
*A61B 17/00* (2006.01)
*A61B 18/14* (2006.01)
*A61B 17/29* (2006.01)

(52) U.S. Cl.
CPC .. *A61B 18/1445* (2013.01); *A61B 2017/2913* (2013.01); *A61B 2017/2916* (2013.01); *A61B 2017/2923* (2013.01); *A61B 2018/1455* (2013.01)

(58) Field of Classification Search
CPC .... A61B 2017/2913; A61B 2017/2916; A61B 2017/2923; A61B 2017/2938; A61B 18/1445; A61B 2018/1455; A61B 34/71; A61B 17/00; A61B 17/072;
(Continued)

(56) References Cited

U.S. PATENT DOCUMENTS 5,542,949 A * 8/1996 Yoon .................. A61B 17/0057
227/901
5,922,001 A * 7/1999 Yoon ................ A61B 17/12013
606/139

(Continued)

FOREIGN PATENT DOCUMENTS

CN 102210608 A 10/2011
CN 102647949 A 8/2012
(Continued)

OTHER PUBLICATIONS

Korean office action in Korean application No. 10-2014-0117653, dated Jul. 11, 2016, 16 pages.
(Continued)

*Primary Examiner* — Gary Jackson
*Assistant Examiner* — Zahed Kabir
(74) *Attorney, Agent, or Firm* — Fitch, Even, Tabin & Flannery LLP (57) ABSTRACT

An instrument (10) according to the invention comprises a cam mechanism drive comprising a locking cam mechanism (31) and a cam mechanism (40), which serves power-transfer and control purposes, so as to initially create a tractive movement at traction elements (20, 21) and then a sliding movement at a sliding element (23). The concept allows for a tolerance-insensitive, functionally reliable design.

13 Claims, 6 Drawing Sheets

(58) Field of Classification Search
CPC ............ A61B 17/2841; A61B 17/2909; A61B 17/07207; A61B 90/03; A61B 2090/065
USPC ................ 601/1; 606/1, 205–208, 142, 143; 227/175.1–182.1
See application file for complete search history.

(56) References Cited

U.S. PATENT DOCUMENTS

| | | | | |
|---|---|---|---|---|
| 6,109,500 | A * | 8/2000 | Alli | A61B 17/07207 227/175.2 |
| 7,641,093 | B2 * | 1/2010 | Doll | A61B 17/07207 227/175.2 |
| 7,753,245 | B2 * | 7/2010 | Boudreaux | A61B 17/07207 227/175.1 |
| 8,747,404 | B2 * | 6/2014 | Boudreaux | 606/207 |
| 8,893,949 | B2 * | 11/2014 | Shelton, IV | A61B 90/92 227/175.1 |
| 2006/0000868 | A1 * | 1/2006 | Shelton, IV | A61B 17/07207 227/175.1 |
| 2007/0078456 | A1 * | 4/2007 | Dumbauld | A61B 18/1445 606/42 |
| 2007/0173814 | A1 * | 7/2007 | Hixson | A61B 18/1445 606/51 |
| 2008/0300613 | A1 | 12/2008 | Shelton, IV et al. | |
| 2009/0112206 | A1 | 4/2009 | Dumbauld et al. | |
| 2009/0209991 | A1 | 8/2009 | Hinchliffe et al. | |
| 2010/0264193 | A1 * | 10/2010 | Huang | A61B 17/068 227/176.1 |
| 2011/0087218 | A1 | 4/2011 | Boudreaux et al. | |
| 2011/0245825 | A1 * | 10/2011 | Mitzlaff | A61B 18/1442 606/37 |
| 2011/0276049 | A1 | 11/2011 | Gerhardt | |
| 2011/0290854 | A1 * | 12/2011 | Timm | A61B 17/072 227/178.1 |
| 2012/0080478 | A1 * | 4/2012 | Morgan | A61B 90/92 227/175.4 |
| 2012/0080493 | A1 * | 4/2012 | Shelton, IV | A61B 17/07207 227/176.1 |
| 2012/0184990 | A1 * | 7/2012 | Twomey | A61B 17/2909 606/206 |
| 2014/0224686 | A1 * | 8/2014 | Aronhalt | A61B 17/068 206/339 |

FOREIGN PATENT DOCUMENTS

| | | |
|---|---|---|
| DE | 4421822 C1 | 10/1995 |
| EP | 2371316 A1 | 10/2011 |
| EP | 2485661 B1 | 10/2013 |
| JP | 2004147701 A | 5/2004 |
| JP | 2009022741 A | 2/2009 |
| JP | 2009078155 A | 4/2009 |
| JP | 2011212446 A | 10/2011 |
| WO | 02/080783 A1 | 10/2002 |
| WO | 2012112622 A2 | 8/2012 |

OTHER PUBLICATIONS

Chinese office action and search report in Chinese application No. 201410457116.8, dated Mar. 2, 2016, 15 pages.
European Search Report in corresponding European Application No. EP13184190.0 dated Jan. 22, 2014, 7 pages.
Japanese office action in corresponding Japanese application No. 2014-182187, dated Dec. 1, 2015, 6 pages.
Japanese search report in corresponding Japanese application No. 2014-182187, dated Nov. 23, 2015, 28 pages.

* cited by examiner

SURGICAL INSTRUMENT COMPRISING AN IMPROVED ACTUATING DRIVE

RELATED APPLICATION(S)

This application claims the benefit of European Patent Application No. EP13183639.7 filed Sep. 10, 2013 and European Patent Application No. EP13184190.0 filed Sep. 12, 2013, the contents of each of which are incorporated herein by reference as if fully rewritten herein.

TECHNICAL FIELD

The invention relates to an instrument, in particular to an electrosurgical instrument, comprising a tool, which comprises members, which are to be actuated consecutively.

BACKGROUND

The term "distal" hereinbelow will always describe the part of the instrument or component, which is located at a distance from the user, the term "proximal" will always describe the part of the instrument or component, which is located closer and which points towards the user.

Such electrosurgical instruments are known from EP 2 371 316 A1, for example. The tool therein is a jaw comprising two branches, at least one of which is pivotably movable. The branch is moved in closing direction by means of a traction element. A blade is displaceably supported between the branches. If the branches are closed, the blade is activated in that it is displaced in distal direction. A sliding element serves to actuate the blade.

The traction element and sliding element are connected to an actuating drive, which is arranged in a housing. An operating lever, which creates the tractive movement for closing the branch on the first part of its movement path and which creates the sliding movement for advancing the blade on the second part of its movement path, is provided as drive. The closing movement in the branch is thereby converted via a toggle joint drive.

There is a desire for improved control of the closing movement and of the force, which acts on the tissue.

SUMMARY

The surgical instrument according to the invention comprises a cam mechanism-type drive for consecutive conversion of the movement of the operating lever into a movement of the traction element and into an opposite movement of the sliding element. The creation of the movement is carried out by means of a cam mechanism and thus opens up broad design options with reference to the relationship of the pivot movement of the operating lever to the closing movement of the branches of a tool. The law of motion is not defined by a toggle joint arrangement, but can be chosen largely freely by selecting the shape of the cam mechanism. In combination with a spring arrangement between the drive and one or a plurality of traction elements for actuating one or both branches, the closing force, which acts between both branches, can be defined accurately and it can be ensured thereby that it is also maintained under different operating conditions with different tissue characteristics.

The actuating lever furthermore comprises a locking cam mechanism, which blocks a movement of the blade as long as the branches are not closed completely. As a whole, this leads to a simple and clear setup and to a reliable function while allowing the tolerances, which are common in plastics technology.

Preferably, the cam mechanism comprises a locking element for blocking a movement of the sliding element in a controlled manner. The locking element can act on the carriage, which serves to actuate the blade. An early or unintentional actuation of the blade can be safely ruled out through this.

Details of advantageous embodiments of the invention follow from the subclaims, the description and/or the drawings.

DETAILED DESCRIPTION

Figures 1, 2, 3:
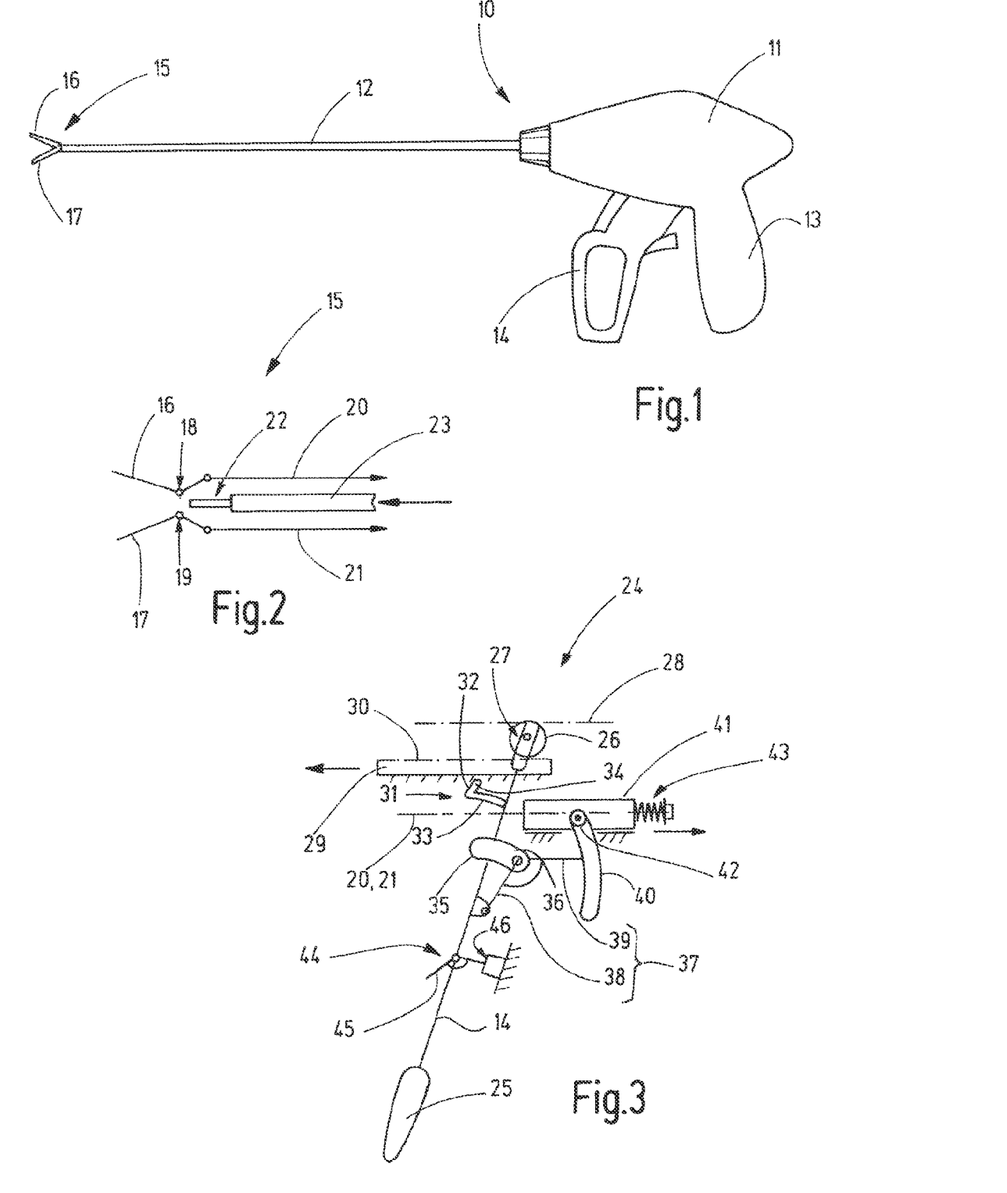
FIG. 1 shows the instrument according to the invention in a general view in a schematic diagram.
FIG. 2 shows the tool of the instrument according to FIG. 1 in a schematic diagram.
FIG. 3 shows the drive of the instrument according to FIG. 1 in a schematic diagram.

FIG. 1 schematically illustrates an instrument 10, which comprises a housing 11 comprising a shaft 12, which extends away from said housing. A handle 13, in the vicinity of which an operating lever 14 is arranged, is embodied at the housing 11.

A tool 15, which comprises two branches 16, 17, is arranged at the distal end of the shaft 12. At least one of said branches it pivotably supported so that the jaw, which is formed between the branches 16, 17, can be opened and closed.

FIG. 2 illustrates this process schematically. The branches 16, 17 of the tool 15 are pivotably supported so as to be capable of being moved towards one another and away from one another by means of suitable pivot bearings 18, 19, which are not shown in detail. For actuation purposes, traction elements 20, 21, which extend through the shaft 12 into the housing 11, connect to the proximal ends of the branches 16, 17.

The tool 15 also includes a blade 22, which is displaceably supported, so as to drive into a straight or curved blade guide groove, which is defined by the branches 16, 17, and to sever tissue seized between the branches 16, 17. The blade 22 thereby cuts with its leading edge, for example, which is oriented at right angles to the direction of movement. It is moved by means of a sliding element 23, which preferably extends between the traction elements 20, 21 through the shaft into the housing 11.

The drive 24, which is arranged in the housing 11, for converting the movement of the operating lever 14 into a tractive movement of the traction elements 20, 21 and into a sliding movement of the sliding element 23, is illustrated separately in a schematic manner in FIG. 3. The operating lever 14 comprises a seizing opening 25 on the bottom. At its other end, it is engaged with a gear wheel 26, which is supported on the operating lever 14 so as to be rotatable and so as to be displaceable in longitudinal lever direction. For accommodating the axle of the gear wheel 26, the operating lever 14 comprises a guide, for example, for the gear wheel, for example in the shape of elongated hole or of a bifurcated end 27.

The gear wheel 26 engages with a gear rod 28, which is embodied so as to be stationary at the housing 11. At its opposite side, the gear wheel 26 is connected to a gear rod 30 of a carriage 29. This gear rod forms a carriage cogging 30, which extends parallel to the gear rod 28. The carriage 29 can be moved parallel to the gear rod 28 and serves to actuate the blade 22. The gear rod 28, the gear wheel 26 and the gear rod 30 of the carriage 29 form a rack and pinion gear.

A locking cam mechanism 31, which comprises two sections 32, 33, which are located at an angle relative to one another, is furthermore embodied at the operating lever 14. A pin 34, which is arranged in the housing 11 so as to be stationary, passes through the locking cam mechanism 31. The locking cam mechanism 31 moves with the operating lever 14 such that the pin 34 is located in the first section 32 in response to the actuation of the branches 16, 17. In response to the actuation of the blade, the pin 34 is in the second section 33.

A first arm 38 of the lever 37 is connected to the operating lever 14 in an articulated manner. The second arm 39 thereof in turn supports a cam mechanism 40, which serves to actuate a carriage 41 for the traction elements 20, 21. The curved cam mechanism 40, which extends quasi at right angles to the second arm 39, guides a cam mechanism journal 42, which is connected to the carriage 41. The carriage 41 is connected to the traction elements 20, 21, which are suggested by means of a dashed line, via a spring element 43, such as a compression spring, for example.

To avoid an undesired actuation of the blade 22, provision is made for a locking device 44. The latter includes one or a plurality of locking levers 45, to which a stop 46 is assigned, which is embodied at the housing 11. The locking lever 45 can be disengaged from the stop 46 by means of manual operation, so as to release the blade movement. In response to an actuation of the operating lever 14, the locking lever 45 then preferably runs against the stop 46, when the pin 34 is located between the two sections 32, 33 of the locking cam mechanism 31.

Figure 4:
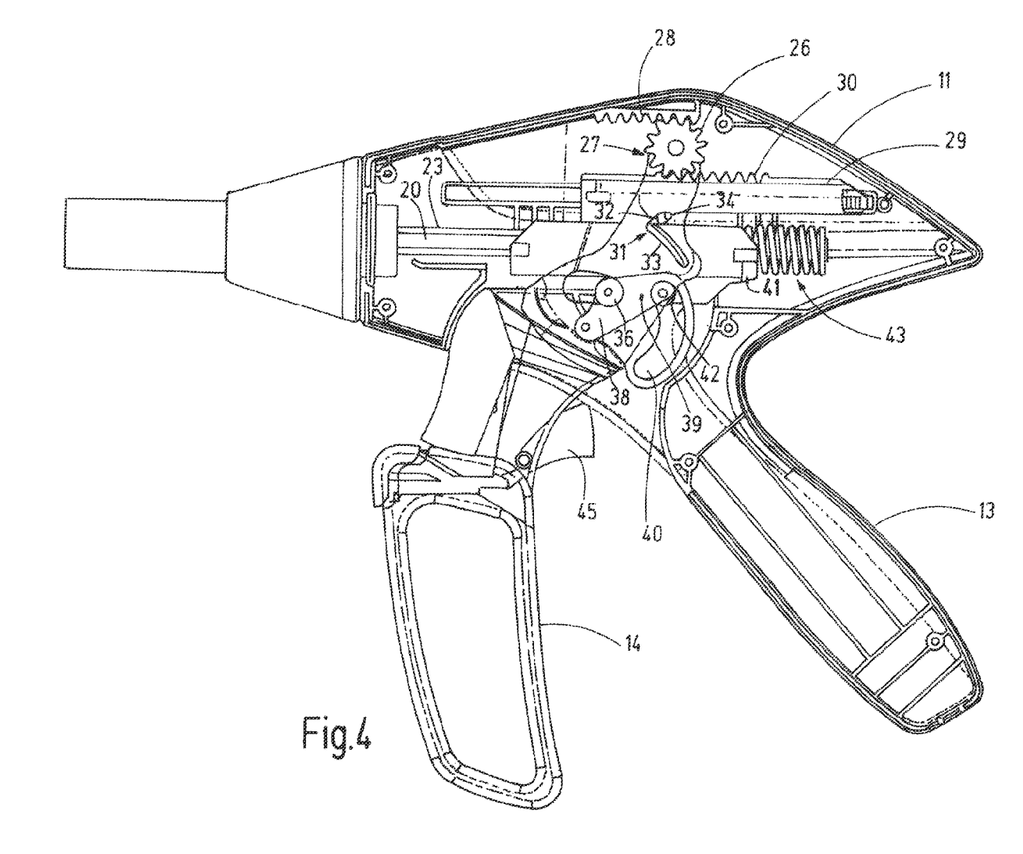
FIG. 4 shows the instrument according to FIG. 1 with open housing in initial position.
Figure 5:
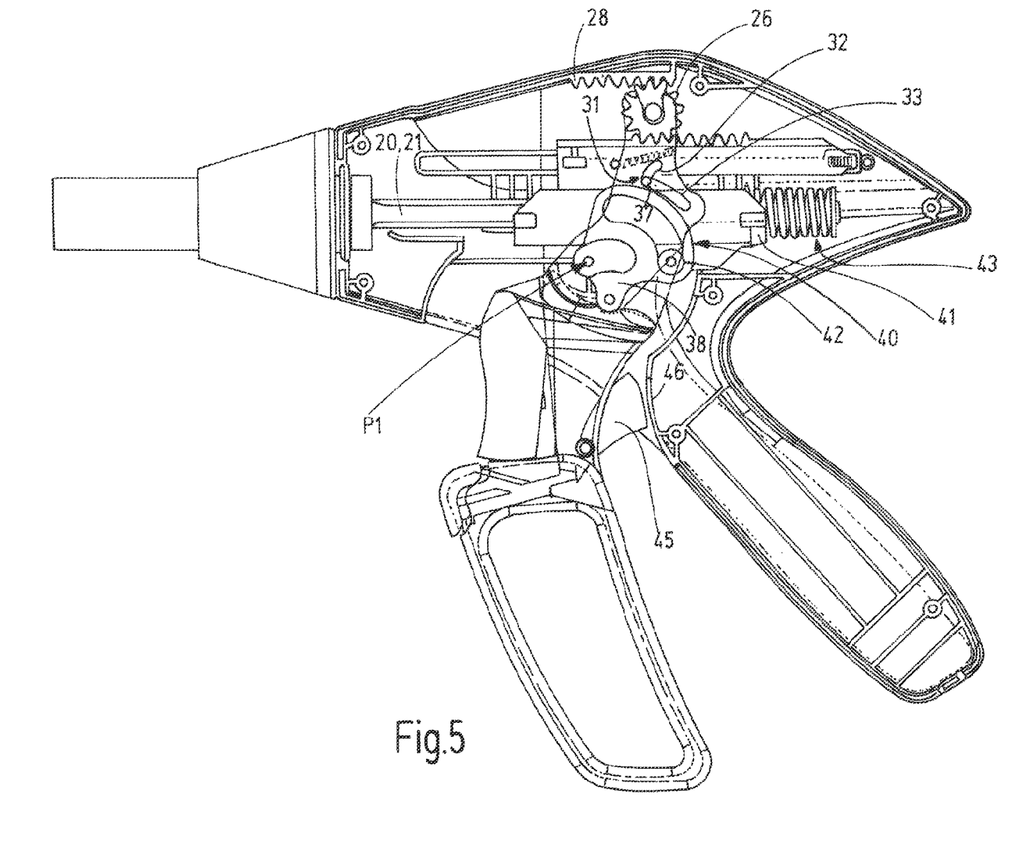
FIG. 5 shows the instrument according to FIG. 4 in the actuating position for the closed tool prior to actuation of the blade.
Figure 6:
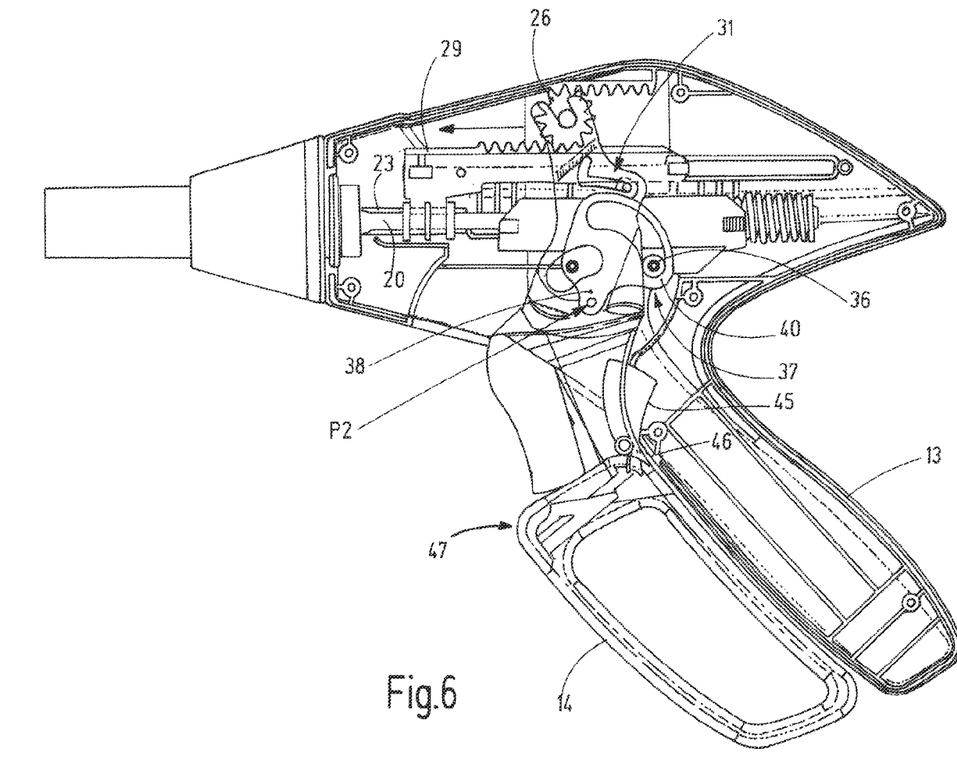
FIG. 6 shows the instrument according to FIGS. 4 and 5 with actuated blade.

Referring to FIGS. 4 to 6 below, the instrument 10 works as follows:

In the initial state, the operating lever 14 is in the distal, that is in FIG. 4, in the left position. It is thereby located such that the locking cam mechanism 31 accommodates the pin 34 with the upper end of its section 32. Both carriages 29, 41 are in the resting position.

When the operating lever 14 is now moved towards the handle 13, the section 32 of the locking cam mechanism 31 keeps the operating lever 14 from noticeably pivoting in distal direction with its upper end. It is thus held at the upper end in the position to the right in FIGS. 4 and 5, that is, on the top in its proximal position, while it carries out a first pivot movement. It is thereby connected via the arm 38 to the center of the cam mechanism journal 36 as (first, provisional) pivot point or center of rotation P1.

Due to the pivot movement of the operating lever 14 the operating lever 14 is displaced slightly in vertical direction (that is, in its longitudinal direction). The locking cam mechanism 31 thus reaches upwards, until the pin 34 is at the angle of the locking cam mechanism 31, that is, between the sections 32, 33. The locking lever 45 thereby strikes against the stop 46 and initially blocks any further movement.

In the above-described first stage of the pivot movement, the pivot movement of the operating lever 14 resulted in that the two-armed lever 37 is pivoted and that the cam mechanism 40 has thus run along its entire length along the cam mechanism journal 42. Due to the fact that the arrangement of the guide track of the cam mechanism 40 along its length has different distances to the center of rotation P1, the carriage 41 has thus been moved in proximal direction, so that the traction elements 20, 21 have transferred a tractive movement onto the tool 15. The law of motion of the carriage movement follows from the suitably defined shape of the cam mechanism 40.

The entire cam mechanism path includes two functions. In the first section, the carriage 41 is moved and the branches 16, 17 are closed. The longitudinal movement of the carriage 41 is a function of the volume of the tissue, which is seized between the branches 16, 17. The branches 16, 17 are clamped in the second section of the cam mechanism path. The lengths of the two sections (displacement or clamping section, respectively) change as a function of the volume of the tissue, which is seized between the branches 16, 17. In the event that no tissue is seized between the branches 16, 17, for example, the section, in which the branches 16, 17 are clamped, only comprises the last area of the cam mechanism path of the cam mechanism 40. In the event that large-volume tissue is seized between the branches 16, 17, the section of the cam mechanism path, which applies the clamping force, can comprise virtually the entire cam mechanism path. The two-armed lever 37, the cam mechanism 40 and the cam mechanism journal 42 form a cam mechanism-type drive. The spring element 43 is pretensioned. It is ensured through this that, after the complete cam mechanism path has been passed through, the tissue seized between the branches 16, 17 is held at a predefined minimum clamping force.

In the event that the user now wants to actuate the blade 22, he must release the locking device 44. For this purpose, he pivots the locking lever 45 away from the stop 46, for example by means of a suitable lever transfer mechanism 47, so that a further movement of the operating lever 14 towards the handle 13 is released.

The cam mechanism 40 is located at the end stop and thus prevents a further pivoting of the two-armed lever 37. The connecting point between the first arm 38 of the lever 37 and the operating lever 14 thus becomes the new center of rotation P2. The locking cam mechanism 31 is also released. This is why the gear wheel 26 moves in distal direction so as to roll along the gear rod 28. Due to the double circumferential speed of the gear wheel 26 with regard to the linear advancing speed thereof, the carriage 29 is conveyed in this direction with twice the speed and accordingly with twice the lift. The sliding element 23 is moved forward very quickly in this manner.

In the case of the presented cam mechanism-type drive, the laws of motion can be designed in a relatively free manner by arranging and embodying the two involved gates 31 and 40 within wide limits. By changing the center of rotation from P1 to P2, additional transmission differences between the actuation of the branches 16, 17 and of the blade 22 can furthermore be created in addition to the differences, which are present otherwise. A movement, which is local and which balances well with regard to force, of the branches 16, 17 and a quick cutting movement of the blade 22 can thus be created.

FIGS. 7 to 10 illustrate a modified embodiment of the instrument 10 according to the invention. Design and function of this instrument 10 is based on the design and the function of the instrument 10 according to FIGS. 1 to 6. The same reference numerals are used as basis and reference is made to the preceding description.

The modification of the instrument 10 according to FIGS. 7 to 10 lies in a locking device 50 for preventing an unintentional actuation of the blade 20. The locking device 50 comprises at least one locking element 51 as well as one or a plurality of actuating elements 52. The locking element 51 is equipped to stop the carriage in its rest position. For this purpose, the locking element 51 can be supported in a displaceable manner, or, as illustrated in the example, in a pivotable manner. At the locking element 51, provision can be made for a locking device 56, which is embodied in the form of a projection, a nose or the like, and which engages with a corresponding recess of the carriage 29 and thus prevents the longitudinal movement of the latter. The center of rotation of the locking element 51 is preferable arranged in a straight extension of the carriage 29.

The actuating element 52 is preferably a manual actuating element, by means of which the locking element can be transferred in a specific manner from its locked position, in which it is engaged with the carriage 29, into a released position. For the manual actuation, provision can be made for rockers, levers, push buttons or rotary knobs or the like, which are attached to the side of the housing.

The locking device 50 can preferably be locked from the outside. The position of the carriage 41, which effects the closing of the tool 15, can be used to stop the locking device 50 in locked position. For this purpose, provision can be made at the locking element 51 for an appendage 58, which, at its end, is embodied as a curve follower element 53. A cam 54, which can be attached to the carriage 41 so as to stick out laterally, is assigned to the curve follower element 53. The curve follower element 53 preferably comprises an inclined surface, which faces the cam 54, and a locking surface, which rests against the cam 54, when the carriage 41 is in initial position (FIG. 7) and when the locking element 51 is in locked position.

In addition, a latching means can be assigned to the locking element 51, so that it remains in each of its two positions, that is, its locked position and its released position, until it is transferred into its respective other position by means of sufficient external forces by overcoming a resistance. Such a latching means can be formed, for example, by means of a latching opening 55 in the latching element and an assigned latching projection 57, which is arranged at the inner side of the housing 11 and across which the locking element 51 must catch so as to reach from one position into its other position. Other latching means, for example in the form of spring-loaded tongues and corresponding recesses, spring-loaded balls, catch spring arrangements and the like, can be used.

Figure 7:
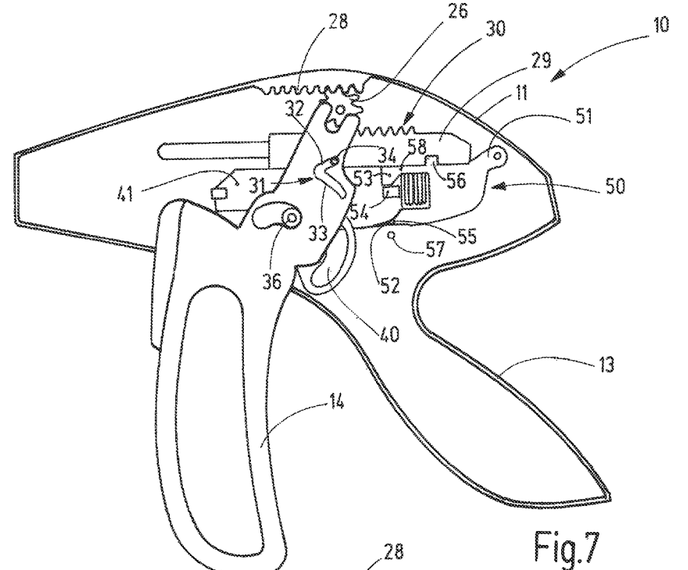
FIG. 7 shows an instrument in modified embodiment with open housing in initial position.

Based on the preceding functional description, the instrument 10 operates as follows according to FIGS. 7 to 10:

The instrument 10 is initially located in the initial state according to FIG. 7. The operating lever 14 is in distal position. The two carriages 29, 41 are in rest position. The locking element 51 is in locked position, in which the locking device 56 engages with a corresponding recess of the carriage 29 and thus stops the latter. With its locking surface, the curve follower element 53 is located on the cam 54. The locking element 51 is thus locked in its locked position. No matter how much he wants to actuate the actuating element 52, a user cannot bring about an unlocking of the carriage 29 and thus also no actuation of the blade.

Figure 8:
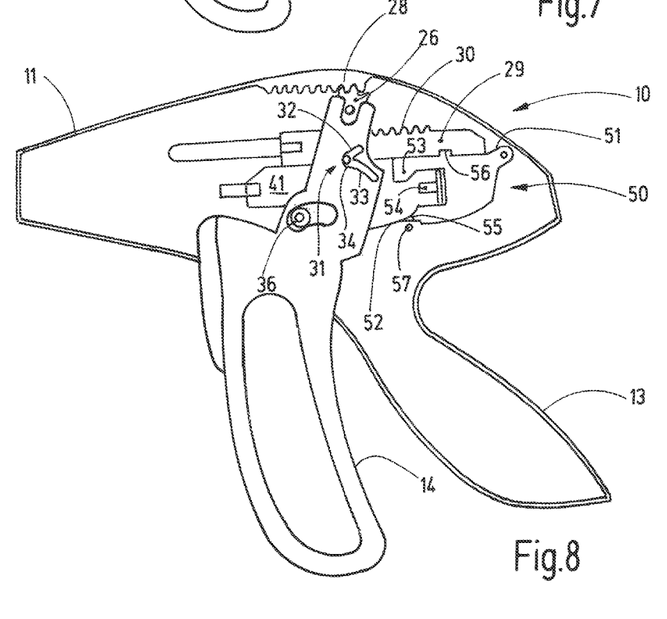
FIG. 8 shows the instrument according to FIG. 7 in actuating position with closed tool and locked blade.

When the operating lever 14 is now moved towards the handle 13 in accordance with FIG. 8, the carriage 29 initially remains in its retracted proximal, that is, non active position. The section 32 of the locking cam mechanism 31 initially hinders the operating lever 14 to pivot noticeably in distal direction with its upper end. However, as described in context with FIGS. 1 to 6, this first movement of the operating lever 14 has the result that the carriage 41 is moved in proximal direction. The tool is thus closed via the traction elements 20, 21. In this first movement phase, the operating lever 14 and thus the locking cam mechanism 31 glide along the first section 32 on the pin 34 towards the gear wheel 26.

When the pin 34 reaches the location of the locking cam mechanism 31, at which the sections 32, 33 meet the locking element 51 initially still prevents a movement of the carriage 29. The locking element 51 blocks a distal movement of the carriage 29 via the latching projection 54. The gear wheel 26 and the upper end of the operating lever 14 are thus also blocked in their movement. The operating lever 14 cannot be moved in the direction of the handle 13 any further.

FIG. 8 illustrates the instrument 10 at the end of this first movement section, in response to which the branches of the tool 15 are closed.

Figure 9:
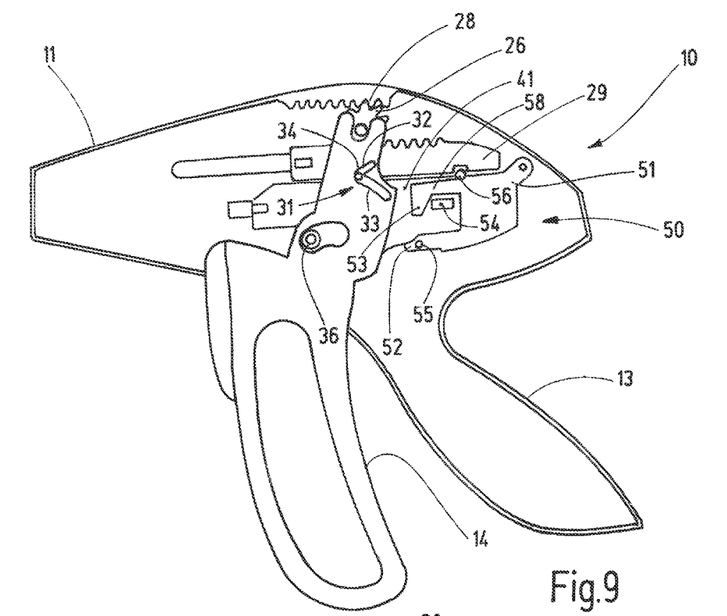
FIG. 9 shows the instrument according to FIG. 7 in actuating position with closed tool and unlocked blade and FIG. 10 shows the instrument according to FIG. 7 in actuating position with closed tool and actuated blade.
Figure 10:
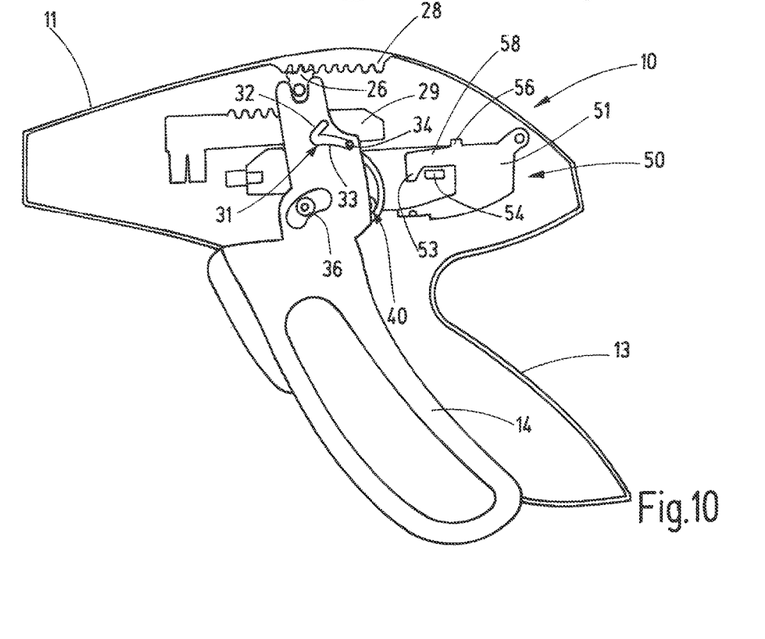

The operator can now release the further movement of the handle 14 and thus the actuation of the blade, in that, by using the actuating element 52, he pivots the locking element 51 out of the locked position into a released position, which is illustrated in FIG. 9. The locking element 51 thereby drives with its latching opening 55 onto the latching projection 57 and locks in place in released position. The locking element 51 now remains in this position. A distal movement of the carriage 29 is released through this. Due to a further movement of the operating lever 14, which is now also released, in the direction of the handle 13, the gear wheel 26 drives in distal direction, unrolling along the gear rod 28. Accordingly, the carriage 29 runs in this direction with twice the stroke. FIG. 9 shows the unlocked locking element 51 of the instrument 10, but prior to actuating the operating lever 14. FIG. 10 illustrates the instrument 10 at the end of the second movement section, during which the blade has been extended.

When the operating lever 14 is now released again by the user, the gear wheel 26 and the carriage 29 now initially move back into its proximal initial position in a spring-supported manner. The system is now again in the situation as in FIG. 9, that is, the locking element 51 is still in released position. A further cut can be made.

However, if the user actively moves the operating lever 14 further in distal direction and if the tool 15 is thus opened, the carriage 41 moves into its distal rest position again. The cam 54 thereby is strikes the inclined surface of the cam follower element 53, which faces it, and pushes the appendage 58 upwards. By overcoming its latching slope, the locking element 51 is thus transferred into the locked position, in which the locking device 56 engages with the recess of the carriage 29. The carriage 29 is thus blocked in rest position again. As an alternative to the illustrated solution, the locking element 51 can also be returned into its initial position via a spring. For example after moving the carriage 29 back, said locking element 51 can already snap upwards as well. Via corresponding contours at the carriage 29 and at the locking element 51, the locking element must be held in released position during the blade movement in this case. Idle positions are unnecessary in this case. In the case of such solutions, however, the actuating element 52 must be held tight at the onset of the movement of the blade.

An instrument 10 according to the invention comprises a cam mechanism-type drive comprising a locking cam mechanism 31 and a cam mechanism 40, which serves power-transfer and control purposes, so as to initially create a tractive movement at traction elements 20, 21 and then a sliding movement at a sliding element 23 consecutively. The concept allows for a tolerance-insensitive, functionally reliable design.

LIST OF REFERENCE NUMERALS 10 instrument
11 housing
12 shaft
13 handle
14 operating lever
15 tool
16, 17 branches
18, 19 pivot bearing
20, 21 traction elements
22 blade
23 sliding element
24 drive
25 seizing opening
26 gear wheel
27 bifurcated end
28 gear rod at the housing 11
29 carriage
30 carriage cogging
31 locking cam mechanism
32, 33 sections of the locking cam mechanism 31
34 pin
36 cam mechanism journal
37 two-armed lever
38 first arm of the lever 37
39 second arm of the lever 37
40 cam mechanism
41 carriage
42 cam mechanism journal
43 spring element
44 locking device
45 locking lever
46 stop
47 lever transfer mechanism
P1 first temporary center of rotation for branch movement
P2 second temporary center of oration for blade movement
50 locking device
51 locking element
52 actuating element
43 cam follower element
54 cam
55 latching opening
56 locking device
57 latching projection
58 appendage

What is claimed is:

1. A surgical instrument (10), comprising:
a tool (15), which comprises at least one movable branch (16, 17) and at least one blade (22), which can be moved linearly,
a shaft (12), which supports the tool (15) at its distal end and through which extend at least one traction element (20, 21) for actuating the branch (16, 17) and a sliding element (23) for actuating the blade (22),
a housing (11), which is connected to a proximal end of the shaft (12),
an operating lever (14) configured to actuate the traction element (20, 21) and the sliding element (23),
wherein the operating lever is configured such that pivoting of the operating lever causes a movement of the traction element to close the at least one movable branch and further pivoting of the operating lever after closing of the at least one movable branch causes movement of the sliding element (23) for actuating the blade (22),
a cam mechanism-type drive (37, 40, 42) configured to convert movement of the operating lever (14) into a sliding movement of the traction element (20, 21),
wherein the cam mechanism-type drive includes a cam mechanism (40) operably connected to a carriage (41), the carriage being operably connected to the traction element such that shifting of the carriage causes a corresponding closing of the at least one moveable branch,
wherein the cam mechanism (40) includes an arcuate camming surface for engaging with a cam journal connected to the carriage, such that pivoting of the operating lever causes the arcuate camming surface to pivot about a first center of rotation (P1) and causes the cam journal of the carriage in engagement with the arcuate camming surface to be shifted in a predetermined direction away from the first center of rotation (P1) to close the at least one movable branch, and
a carriage (29) in operable engagement with the sliding element to shift the sliding element to actuate the blade;
a locking device (50) selectively engageable with the carriage to block movement of the carriage, wherein the locking device is shiftable between a locked position, wherein the locking device directly engages the carriage to block movement of the carriage, and a released position, wherein the locking device is out of engagement with the carriage to allow the carriage to be shifted to shift the sliding element for actuating the blade;
wherein the locking device (50) includes a locking element (51) in the form of a projection to engage a corresponding recess in the carriage (29) to block movement of the carriage when the locking device is in the locked position with the locking element in direct engagement with the carriage recess for blocking a movement of the sliding element (23).

2. The instrument according to claim 1, further comprising a gear rod drive (28, 26, 30) configured to convert a pivot movement of the operating lever (14) into a sliding movement of the sliding element (23).

3. The instrument according to claim 1, further comprising a two-armed lever (37), which can be pivoted about a bearing, which is stationary relative to the housing (11) and which defines the first center of rotation (P1), wherein the two-armed lever (37) is part of the cam mechanism-type drive (37, 40, 42).

4. The instrument according to claim 3, wherein the two-armed lever (37) comprises a first arm (38), which is connected in an articulated manner to the operating lever (14).

5. The instrument according to claim 3, wherein the two-armed lever (37) comprises a second arm (39) including the cam mechanism (40).

6. The instrument according to claim 1, wherein the operating lever (14) is connected to a gear wheel (26), which engages with a gear rod (28), which is stationary relative to the housing (11).

7. The instrument according to claim 6, wherein the gear wheel (26) engages with a linear carriage cogging (30) of the carriage (29), wherein the linear carriage cogging runs parallel to the gear rod (28), such that the carriage is capable of being displaced parallel to the gear rod (28).

8. The instrument according to claim 1, wherein the actuating stroke of the carriage (41), which is operably connected to the branches (16, 17), is limited by an arrangement of the cam mechanism (40).

9. The instrument according to claim 1, wherein the carriage (41), which is operably connected to the branches (16, 17), is connected to the traction elements (20, 21) via a spring element (43).

10. The instrument according to claim 1, further comprising a locking device (44), which defines a locking point to limit movement of the operating lever (14) to a partial path.

11. The instrument according to claim 1, wherein the cam mechanism drive (37, 40, 42) is embodied so as to assign two different temporary centers of rotation (P1, P2) to the operating lever (14), wherein the temporary center of rotation corresponds to the first center of rotation (P1) and is assigned to movement of the branches (16, 17) and another center of rotation (P2) is assigned to movement of the blade (22).

12. The instrument according to claim 1, wherein the locking device includes a manual actuating element (52) to shift the locking device between the locked and released positions.

13. The instrument according to claim 12, wherein the manual actuating element includes a lever extending from the housing to shift the locking device between the locked and released positions.

\* \* \* \* \*

UNITED STATES PATENT AND TRADEMARK OFFICE
CERTIFICATE OF CORRECTION

PATENT NO. : 10,123,834 B2
APPLICATION NO. : 14/482901
DATED : November 13, 2018
INVENTOR(S) : Elias Schiele et al.

Page 1 of 1

It is certified that error appears in the above-identified patent and that said Letters Patent is hereby corrected as shown below:

On the Title Page

Column 1, Line 6, delete "Gieslingen (DE)" and insert --Geislingen (DE).--

Signed and Sealed this
Eleventh Day of December, 2018

Andrei Iancu
*Director of the United States Patent and Trademark Office*